US006414188B1

(12) United States Patent
Vigil et al.

(10) Patent No.: US 6,414,188 B1
(45) Date of Patent: Jul. 2, 2002

(54) METHOD OF PREPARING AMINO-, IMINO-, AND NITRILOCARBOXYLIC ACIDS AND SILVER-PROMOTED COPPER CATALYST FOR USE IN SAID METHOD

(75) Inventors: Jorge Gustavo Vigil; Marta Del Carmen Ruiz, both of Llavallol (AR)

(73) Assignee: Atanor S.A., Buenos Aires (AR)

( * ) Notice: Subject to any disclaimer, the term of this patent is extended or adjusted under 35 U.S.C. 154(b) by 0 days.

(21) Appl. No.: 09/541,692

(22) Filed: Apr. 3, 2000

(30) Foreign Application Priority Data

Jul. 5, 1999 (AR) .......................................... 990103248

(51) Int. Cl.⁷ .............................................. C07C 51/23
(52) U.S. Cl. ....................................... 562/526; 562/523
(58) Field of Search ................................ 562/503, 505, 562/506, 523, 512, 526; 502/301, 345

(56) References Cited

U.S. PATENT DOCUMENTS

| 2,384,816 A | | 9/1945 | Curme, Jr. et al. ......... 260/531 |
| 2,384,817 A | | 9/1945 | Chitwood .................... 260/531 |
| 2,939,883 A | * | 6/1960 | Punderson |
| 2,944,946 A | * | 7/1960 | Lane |
| 3,126,273 A | * | 3/1964 | Justi et al. |
| 3,578,709 A | | 5/1971 | Bishop et al. ............... 260/534 |
| 3,842,081 A | | 10/1974 | Schulze et al. ............. 260/268 |
| 3,844,981 A | * | 10/1974 | Cusumano |
| 4,233,246 A | * | 11/1980 | Dudeck et al. ............. 568/402 |
| 4,782,183 A | | 11/1988 | Goto et al. .................. 562/526 |
| 5,039,649 A | * | 8/1991 | Lippert et al. .............. 502/301 |
| 5,225,592 A | | 7/1993 | Ochoa Gomez ............ 562/526 |
| 5,292,936 A | * | 3/1994 | Franczyk ..................... 562/526 |
| 5,367,112 A | | 11/1994 | Franczyk .................... 562/526 |
| 5,689,000 A | * | 11/1997 | Ebner et al. ................ 562/539 |

FOREIGN PATENT DOCUMENTS

| WO | WO92/06069 | 4/1992 |

* cited by examiner

*Primary Examiner*—Jean F. Vollano
(74) *Attorney, Agent, or Firm*—Jacobson Holman, PLLC

(57) ABSTRACT

Disclosed herein is a method for preparing amino-, imino-, and nitrilocarboxylic acids, and their alkali metal salts, starting from alkanolamines. The method employs oxidative dehydrogenation of the alkanolamine(s) in an alkali metal hydroxide medium, using a copper catalyst containing silver. The subject amino-, imino-, and nitrilocarboxylic acids have the following formula: R1R2R3 N where R3 is an alkyl group having 1–10 C atoms substituted with a carboxyl group (—COOH), R1 and R2, which may be the same or different, represent hydrogen, an alkyl group having 1–10 C atoms, an alkyl group having 1–10 C atoms substituted with a carboxyl group, a cycloalkyl group having 3–6 C atoms substituted with a carboxyl group, a cycloalkyl-alkyl group having 3–6 C atoms in the cycloalkyl moiety and 1–10 C atoms in the alkyl moiety and substituted with a carboxyl group, or an alkyl-cycloalkyl group having 1–10 C atoms in the alkyl moiety and 3–6 C atoms in the cycloalkyl moiety and substituted with a carboxyl group; wherein said alkyl groups may be linear or branched.

7 Claims, No Drawings

METHOD OF PREPARING AMINO-, IMINO-, AND NITRILOCARBOXYLIC ACIDS AND SILVER-PROMOTED COPPER CATALYST FOR USE IN SAID METHOD

SUMMARY OF THE INVENTION

A method is described for preparing amino-, imino-, and nitrilocarboxylic acids, and their alkali metal salts, starting from alkanolamines. The method employs oxidative dehydrogenation of the alkanolamine(s) in an alkali metal hydroxide medium, using a copper catalyst containing silver.

The subject amino-, imino-, and nitrilocarboxylic acids have the following formula:

$$R_1R_2R_3N \qquad (I)$$

where R3 is an alkyl group having 1–10 C atoms substituted with a carboxyl group (—COOH), R1 and R2, which may be the same or different, represent:
hydrogen,
an alkyl group having 1–10 C atoms,
an alkyl group having 1–10 C atoms substituted with a carboxyl group,
a cycloalkyl group having 3–6 C atoms substituted with a carboxyl group,
a cycloalkyl-alkyl group having 3–6 C atoms in the cycloalkyl moiety and 1–10 atoms in the alkyl moiety and substituted with a carboxyl group,
or an alkyl-cycloalkyl group having 1–10 atoms in the alkyl moiety and 3–6 atoms in the cycloalkyl moiety and substituted with a carboxyl group;
wherewith said alkyl groups may be linear or branched,
The described method comprises the following:
(a) Subjecting alkanolamines of formula $$R_1'R_2'R_3'N \qquad (II)$$

wherein the R' groups have the same substituents as set forth above for the R groups, except that the aforesaid carboxyl groups (—COOH) are —CH2OH groups, to an oxidative dehydrogenation reaction in aqueous alkali metal hydroxide medium in the presence of a copper catalyst containing 50–5000 ppm of silver as a promoter;
(b) separating the resulting carboxylate salts from the reaction medium, and optionally purifying said salts or converting them to the corresponding amino acids by precipitation in acid medium;
(c) separating the catalyst from the reaction medium, washing said catalyst with demineralized water, and optionally recycling the catalyst to re-use in step (a), of the same or another production run; and
(d) recovering and collecting the hydrogen liberated in the reaction.

The compounds of formula (I) have been found to be important synthesis intermediaries, e.g. in preparation of N-phosphonomethylglycine (the herbicidal agent known as glyphosate). In our invention, the copper catalyst containing silver as a promoter (e.g. via silver salts), has the advantage that reactivation with each re-use of the catalyst is not required. If a copper catalyst without silver is used, or if a copper catalyst containing a metal or metals other than silver e.g., chromium, nickel, molybdenum, tungsten, vanadium, titanium, niobium, manganese, zirconium, cobalt, or mixtures of these is used, the catalyst activity fades rapidly with successive reactions.

For the better part of 200 years, it has been known to convert alcohols to alkali metal salts of the corresponding carboxylic acids by heating the alcohols with alkali metal hydroxides (Dumas, 1840, 35 Ann. 129–73).

The reaction has been extended to aminoalcohols; when these are heated in the presence of an alkali metal compound they undergo oxidative dehydrogenation to yield the alkali metal salt of the corresponding amino- or iminoacid; this occurs even without a catalyst (U.S. Pat. No. 2,384,816, preparation of glycine in low yield from diethanolamine and KOH). Known catalysts for use with this reaction include, e.g., cadmium oxide, zinc oxide, palladium, platinum, and activated copper. Hydrogen is liberated. Oxygen or a gas containing oxygen may be introduced to form water from the hydrogen and thereby avoid hazardous accumulations of hydrogen.

DESCRIPTION OF THE RELATED ART

Examples from the Patent Literature:

U.S. Pat. No. 2,384,817 (1945), preparation of glycine from monoethanolamine (MEA) and potassium hydroxide at elevated temperature, in an anhydrous medium, with an activated copper catalyst (low yield);

U.S. Pat. No. 3,842,081 (1974), preparation of iminodiacetic acid (IDA) from diethanolamine (DEA) and potassium hydroxide, with a cadmium oxide catalyst (good yield, but cadmium is deemed a toxic substance);

U.S. Pat. No. 3,578,709 (1971), preparation of nitrilotriacetic acid (NTA) from triethanolamine (TEA) and an alkali metal hydroxide, with a zinc oxide catalyst (low yield);

Jap. Pat. 53/7709, preparation of IDA and NTA from DEA and TEA, respectively, in a sodium oxide medium, with a catalyst comprised of Pd or Pt supported on carbon, with injection of oxygen or a gas containing oxygen (low yields, on the order of 70%, and costly precious metal catalysts used to produce a product of relatively low net value);

U.S. Pat. No. 4,782,183, preparation of glycine, IDA, and NTA, from MEA, DEA, and TEA, respectively, and a hydroxide of an [alkaline] alkali metal in aqueous medium, with an activated copper catalyst, at pressures up to 980 kPa (conversion very good), as in the preceding examples, hydrogen liberated in the amount of 2 hydrogen atoms per acetic group, and the further disadvantage pertains that the copper cannot be re-used but must be replaced by fresh copper for each synthesis run, because it becomes depleted (poisoned) in a single use;

U.S. Pat. No. 5,367,112 (1994), preparation of glycine, IDA, and NTA, from MEA, DEA, and TEA, respectively, under the same conditions as in the above-cited patent, but wherewith the activated copper catalyst is promoted with 50–10,000 ppm of an element selected from the group comprising chromium, titanium, niobium, tantalum, tungsten, zirconium, vanadium, molybdenum, manganese, cobalt, nickel, or a mixture of these, the concentration of the catalyst being very high, viz. double that used according to U.S. Pat. No. 4,782,183;

U.S. Pat. No. 5,225,592 (1993), preparation of glycine, IDA, and NTA, from the corresponding alkanolamines and sodium hydroxide, with a copper catalyst, all in aqueous medium and with injection of oxygen or an oxygen-containing gas to avoid emission of hydrogen, the avoidance being achieved viz. by formation of water with the oxygen. Pressure of the system maintained at values up to 11,765 kPa. Drawback again that a new catalyst must be used for each synthesis run;

(PTO Pat. App.) WO 92/06069, regeneration of activated copper used as a catalyst in synthesis of acetic acid derivatives, e.g. preparation of glycine, IDA, and NTA via oxidative dehydrogenation of MEA, DEA, and TEA, respectively. The regeneration is needed because the catalyst loses substantial activity, wherewith in practice absent regeneration it cannot be used more than once and therefore is not economical for industrial applications. In the regeneration, after each synthesis run the copper is treated in an aqueous solution of formaldehyde. A drawback is that effluents resulting from formaldehyde solutions are bactericidal, which creates a disposal problem, not necessary with our invention.

DETAILED DESCRIPTION OF THE INVENTION

As mentioned above, the above-described copper catalysts, possibly promoted with chromium, molybdenum, titanium, niobium, tantalum, vanadium, zirconium, manganese, tungsten, cobalt, nickel, or with mixtures of these, all experience an appreciable loss of activity with successive uses after the first synthesis run, necessitating re-activation. The loss of activity is attributable to formation of cuprous and cupric oxides on the surface of the copper particles.

It was discovered, in connection with the present invention, that the herein described incorporation of silver in the copper catalyst will greatly increase the catalyst yield as well as substantially increasing the number of synthesis runs for which the catalyst can be used and re-used. Moreover, savings in catalyst used of up to 50 % can be achieved in comparison to the amounts needed according to the above-described prior art patents. The effect is believed to be due to electrochemical protection of the copper by the silver, which reduces or prevents oxidation of the copper. This protective effect, which can be observed by the naked eye as a simple color change if the catalyst is used without a promoter, in comparison to no color change in the promoted catalyst, was clearly established by examination in an electron microscope at magnifications of 150× and 5000×. Particles of un-promoted copper catalyst, and particles of copper catalyst containing silver as a promoter, as described in the present patent application, were subjected to such an examination before and after use, which examination revealed significant differences in the appearance of the un-promoted compared to the promoted activated copper, which stemmed from structural differences in the particles. The micrographs of the copper without the promoter taken before and after use of the catalyst appeared very different: the unused particles had a surface which, while irregular, had a uniform and continuous surface appearance, whereas the used particles showed areas of reduced thickness, with deep fissures and meandering depressions. In contrast, the silver-copper particles had nearly the identical appearance before and after use, indicating a chemical and electrochemical protective effect of the silver on the copper. Consequently, the copper catalyst containing silver had a longer service life than the copper catalyst without silver as a promoter.

The aminoalcohols which may be used in the context of the claimed method are:

MEA, DEA, TEA, N-methylethanolamine,

N-ethylethanolamine, N-ispropylethanolamine, N-butylethanolamine, nonylethanolamine, N-(2-aminoethyl)ethanolamine, N-(3-aminopropyl)ethanolamine, N,N-dimethylethanolamine, N,N-diethylethanolamine, N,N-dibutylethanolamine, N-methyl-N,N-diethanolamine, N-ethyl-N,N-diethanolamine, N-isopropyl-N,N-diethanolamine, N-butyl-N,N-diethanolamine, N-ethyl-N-(2-aminoethyl)ethanolamine, and N-methyl-N-(3-aminopropyl)ethanolamine.

The initial concentration of the alkanolamines may be in the range 15–35 wt % based on the total initial weight of the reaction components, preferably 26–30 wt %. For concentrations above 30 wt %, solubility problems may be encountered, and for concentrations below 26 wt %, correspondingly lower productivity is experienced.

The silver-copper catalyst is first obtained by treating an Al—2Cu alloy with sodium hydroxyde, by methods which are per se known. The silver promoter can be incorporated in the alloy; or is applied by precipitation on the catalytic copper by treatment in alkaline medium, from silver salts such as the nitrate, fluoride, chlorate, per chlorate, or lactate, or is provided via simple mixture of activated copper with 50–5000 ppm of finely divided metallic silver.

The amount of catalyst added is in the range 5–25 wt % based on the weight of the alkanolamine to be reacted, preferably 8–12 wt %. At these concentrations, better results are obtained than with un-promoted copper catalyst, or with a copper catalyst promoted with chromium, vanadium, titanium, molybdenum, tungsten, manganese, cobalt, nickel, niobium, tantalum, and zirconium, or mixtures of these.

The solvent is water, to which an alkaline hydroxide has been added in a molar ratio with respect to the alkanolamine which is in the range (stoichiometric) to (stoichiometric +15%); preferably the alkaline hydroxide is added in a stoichiometric amount or in a 5% molar excess. The hydroxide may be that of any alkali metal (e.g. lithium, sodium, or potassium), provided that the salts of said hydroxide with the synthesized amino acid are soluble in the reaction medium at the synthesis temperature and pressure.

The reaction is carried out at 100–220° C., preferably 120–190° C., at a pressure in the range 490–1470 kPa, preferably 784–1170 kPa, particularly preferably 883–980 kPa.

The conversion of the alkanolamine to the corresponding amino acid occurs with liberation of hydrogen. The hydrogen may be compressed and stored for use in other processes.

The invention will be illustrated by way of the following Examples.

EXAMPLE 1

(Comparison Example)

In this Example, the results obtained are those from a method of preparing an amino acid from an alkanolamine, wherewith the catalyst used is a copper catalyst which is not promoted with another metal.

Into a 3.5 L pressure reactor comprised of type "316" stainless steel and having an agitator, there were charged:

1070 g (10 mol) 99% diethanolamine (DEA);

1739 g (20 mol) 46 wt % aqueous NaOH;

2033 g demineralized water; and 115.5 g (dry basis) copper catalyst (comprising 210 g of 55 wt % copper prepared in water).

With the reactor hermetically sealed, the mixture was heated to a point of temperature 120° C., pressure 980 kPa, at which time purging of the $H_2$ produced was begun, in a manner such that the temperature rose to 160–180° C., with the pressure being maintained at 882–980 kPa. The reaction was continued under these conditions of temperature and pressure, with agitation, until no further hydrogen appeared to be emitted (based on monitoring), which took 4 hr. Continuing the agitation, the resulting solution of sodium iminodiacetate with suspended activated copper was cooled to 70° C. The solution of sodium iminodiacetate was separated out and the catalytic copper was washed with demineralized water, fresh copper catalyst in the amount of 2.5 wt % was added (dry basis) (0.025×the 115.5 g originally employed) to compensate for the losses in handling, and the copper catalyst prepared was then re-used in a new synthesis.

The procedure was repeated, thereby testing the catalyst in 1 initial and 2 re-uses.

The results are set forth in Table 1.

TABLE 1

Conversion of DEA to IDA (iminodiacetic acid), in a number of synthesis runs, using and re-using as catalyst the same copper catalyst:

| Synthesis run | Conversion to IDA (%) | Reaction time (hr) |
|---|---|---|
| 1 | 99.8 | 4.0 |
| 2 | 88.7 | $4.5^1$ |
| 3 | 68.2 | $5.0^1$ |

[1]After this period of time, the reaction rate had slowed to essentially zero, with no more hydrogen being liberated, wherewith the intermediate formed, which was present at that time, was not catalyzed to be finally converted to IDA.

EXAMPLE 2

The process was carried out with the same equipment, the same concentrations of raw materials, and the same conditions of pressure and temperature as in Example 1, but the copper catalyst employed was promoted with 1000 ppm chromium, which was incorporated in an alloy, Al—2Cu. The results of the experiments are presented in Table 2.

TABLE 2

Conversion of DEA to IDA (iminodiacetic acid), in a number of synthesis runs, using and re-using as catalyst the same copper catalyst (promoted with 1000 ppm chromium incorporated in an alloy Al—2Cu):

| Synthesis run | Conversion to IDA (%) | Reaction time (hr) |
|---|---|---|
| 1 | 99.5 | 4.5 |
| 2 | 70 | $5.0^1$ |

[1]After this period of time, the reaction rate had slowed to essentially zero, with no more hydrogen being liberated, wherewith the intermediate formed, which was present at that time, was not catalyzed to be finally converted to IDA.

EXAMPLE 3

The process was carried out with the same equipment, the same concentrations of raw materials, and the same conditions of pressure and temperature as in Example 1, but the copper catalyst employed in each synthesis run was promoted with 100 ppm chromium, which was added as chromium nitrate. The results of the experiments are presented in Table 3.

TABLE 3

Conversion of DEA to IDA (iminodiacetic acid), in a number of synthesis runs, using and re-using as catalyst in each synthesis run the same copper catalyst (promoted with 100 ppm chromium which was added as chromium nitrate):

| Synthesis run | Conversion to IDA (%) | Reaction time (hr) |
|---|---|---|
| 1 | 99.9 | 4.5 |
| 2 | 91.8 | $5.0^1$ |
| 3 | 84 | $5.7^1$ |
| 4 | 68 | $6^1$ |

[1]After the stated period of time, the reaction rate had slowed to essentially zero, with no more hydrogen being liberated, wherewith the intermediate formed, which was present at that time, was not catalyst to be finally converted to IDA.

EXAMPLE 4

The process was carried out with the same equipment, the same concentrations of raw materials, and the same conditions of pressure and temperature as in Example 1, but the copper catalyst employed was promoted with 1000 ppm silver, which was added in the form of silver nitrate in the first synthesis run.

The results of the experiments are presented in Table 4.

TABLE 4

Conversion of DEA to IDA (iminodiacetic acid), in a number of synthesis runs, using and re-using as catalyst the same copper catalyst (promoted with 1000 ppm silver which was added in the form of silver nitrate):

| Synthesis run | Conversion to IDA (%) | Reaction time (hr) |
|---|---|---|
| 1 | 96.8 | 4.5 |
| 2 | 92.0 | $5^1$ |
| 3 | 89.6 | $5.5^1$ |
| 4 | 90.3 | $5.5^1$ |
| 5 | 88.9 | $5.3^1$ |
| 8 | 90.0 | $5.6^1$ |
| 10 | 89.1 | $5.5^1$ |

[1]After this period of time, the reaction rate had slowed to essentially zero, with no more hydrogen being liberated, wherewith the intermediate formed, which was present at that time, was not catalyzed to be finally converted to IDA.

EXAMPLE 5

The process was carried out with the same equipment, the same concentrations of raw materials and the same conditions of pressure and temperature as in Example 1, but the copper catalyst employed was promoted with 1000 ppm silver, which was added in the form of silver flouride in the first synthesis run.

The results are presented in Table 5.

TABLE 5

Conversion of DEA to IDA (iminodiacetic acid), in a number of synthesis runs, using and re-using as catalyst the same copper catalyst (promoted with 1000 ppm silver which was added in the form of silver fluoride):

| Synthesis run | Conversion to IDA (%) | Reaction time (hr) |
|---|---|---|
| 1 | 93.5 | 4.0[1] |
| 2 | 91.7 | 4.6[1] |
| 3 | 88.6 | 5.0[1] |
| 4 | 90.4 | 4.8[1] |
| 5 | 88.4 | 5.1[1] |
| 8 | 90.3 | 5.3[1] |
| 10 | 89.3 | 5.1[1] |

[1]After this period of time, the reaction rate had slowed to essentially zero, with no more hydrogen being liberated, wherewith the intermediate formed, which was present at that time, was not catalyzed to be finally converted to IDA.

EXAMPLE 6

Into a 15 L pressure reactor comprised of type "316" stainless steel and having an agitator, there were charged:

2921 g (27.3 mol) 99% diethanolamine (DEA);

4747.5 g (54.6 mol) 46 wt % aqueous NaOH;

5550 g demineralized water; and 315.3 g (dry basis) copper catalyst, promoted with 1000 ppm silver added during the formation of an aluminum alloy, Al—2Cu.

With the reactor hermetically sealed, the mixture was heated to a point of temperature 120° C., pressure 980 kPa, at which time purging of the H2 produced was begun, in a manner such that the temperature rose to 160–180° C., with the pressure being maintained at 882–980 kPa. The reaction was continued under these conditions of temperature and pressure, with agitation, until no further hydrogen appeared to be emitted based on monitoring. This practical end point was reached in 4.2 hr in the first synthesis run; the tenth synthesis run took 25% more time. Continuing the agitation, the resulting solution of sodium iminodiacetate with suspended activated copper was then cooled to 70° C. The solution of sodium iminodiacetate was separated out and the copper catalyst was washed with demineralized water, fresh copper catalyst in the amount of 2.5 wt % was added (dry basis) (0.025×the 315.3 g originally employed) to compensate for the losses in handling, and the copper catalyst mixture was then re-used in a new synthesis. The procedure was repeated, thereby testing the catalyst in 1 initial and 9 re-uses. The results are set forth in Table 6.

TABLE 6

Conversion of DEA to IDA (iminodiacetic acid), in a number of synthesis runs, using and re-using as catalyst the same copper catalyst (promoted with 1000 ppm silver added during the formation of an aluminum alloy, Al—2Cu):

| Synthesis run | Conversion to IDA (%) | Reaction time (hr) |
|---|---|---|
| 1 | 96.0 | 4.2 |
| 2 | 93.4 | 4.5 |
| 3 | 90.5 | 4.9[1] |
| 4 | 90.6 | 4.8[1] |
| 5 | 89.7 | 5.0[1] |
| 8 | 87.5 | 4.9[1] |
| 10 | 90.1 | 5.4[1] |

[1]After this period of time, the reaction rate had slowed to essentially zero, with no more hydrogen being liberated, wherewith the intermediate formed, which was present at that time, was not catalyzed to be finally converted to IDA.

EXAMPLE 7

The process was carried out with the same equipment, the same concentrations of raw materials, and the same conditions of pressure and temperature, with agitation, as in Example 6, but the copper catalyst employed was promoted with 1000 ppm silver, which was added in granular form in the first synthesis run. The results are presented in Table 7.

TABLE 7

Conversion of DEA to IDA (iminodiacetic acid), in a number of synthesis runs, using and re-using as catalyst the same copper catalyst (promoted with 1000 ppm silver which was added in granular form):

| Synthesis run | Conversion to IDA (%) | Reaction time (hr) |
|---|---|---|
| 1 | 95.5 | 4.5 |
| 2 | 93.1 | 5.0 |
| 3 | 90.1 | 5.5[1] |
| 4 | 90.0 | 5.6[1] |
| 5 | 88.5 | 5.6[1] |
| 8 | 87.0 | 5.5[1] |
| 10 | 89.8 | 5.8[1] |

[1]After this period of time, the reaction rate had slowed to essentially zero, with no more hydrogen being liberated, wherewith the intermediate formed, which was present at that time, was not catalyzed to be finally converted to IDA.

We claim:

1. A method of preparing amino-, imino-, and nitrilocarboxylic acids of formula $$R1R2R3\,N \qquad (I)$$

and alkali metal salts of these, wherein R3 is an alkyl group having 1–10 C atoms substituted with a carboxyl group (—COOH), R1 and R2, which may be the same or different, represent:

hydrogen, an alkyl group having 1–10 C atoms, an alkyl group having 1–10 C atoms substituted with a carboxyl group, a cycloalkyl group having 3–6 C atoms substituted with a carboxyl group, a cycloalkyl-alkyl group having 3–6 C atoms in the cycloalkyl moiety and 1–10 atoms in the alkyl moiety and substituted with a carboxyl group, or an alkyl-cycloalkyl group having 1–10 atoms in the alkyl moiety and 3–6 atoms in the cycloalkyl moiety and subtituted with a carboxyl group;

wherein said alkyl groups may be linear or branched, which comprises:

(a) subjecting alkanolamines of formula

  (II)

wherein the R' groups have the same significations as set forth above for the R groups, except that the aforesaid carboxyl groups (—COOH) are —CH2OH groups, to an oxidative dehydrogenation reaction in aqueous alkali metal hydroxide medium in the presence of a copper catalyst containing 50–5000 ppm of silver as a promoter;

(b) separating the resulting carboxylate salts from the reaction medium, and optionally purifying said salts or converting them to the corresponding amino acids by precipitation in acid medium;

(c) separating the catalyst from the reaction medium, washing said catalyst with demineralized water, and recycling the catalyst to re-use in step (a), of the same or another production run; and (d) recovering and collecting the hydrogen liberated in the reaction.

2. A method according to claim 1, wherein the initial concentration of the alkanolamine in the reaction step is in the range 15–35 wt % based on the total weight of the reaction components.

3. A method according to claim 1, wherein the reaction is carried out at a temperature in the range of 100–200° C.

4. A method according to claim 1, wherein the reaction is carried out at a total pressure in the range of 490–1470 kPa.

5. A method according to claim 1, wherein the reaction is carried out in the presence of an alkali metal hydroxide which is present in a molar amount with respect to the alkanolamine in the range of (stoichiometric) to (stoichiometric +15%).

6. A method according to claim 1, wherein the amount of catalyst provided in the reaction step is in the range of 5–25 wt % based on the weight of the alkanolamine.

7. A method according to claim 2 wherein the initial concentration of the alkanolamine in the reaction step is in the range or 26–30 wt% based on the total weight of the reaction components.

* * * * *